United States Patent
Bruce et al.

(10) Patent No.: US 8,750,967 B2
(45) Date of Patent: Jun. 10, 2014

(54) MEDICAL FLUID DELIVERY SYSTEM WITH RFID-EQUIPPED WAND

(75) Inventors: John K. Bruce, Burlington, KY (US);
Chad M. Gibson, Westerville, OH (US);
Geoffrey S. Strobl, Williamsburg, OH (US)

(73) Assignee: Mallinckrodt LLC, Hazelwood, MO (US)

( * ) Notice: Subject to any disclaimer, the term of this patent is extended or adjusted under 35 U.S.C. 154(b) by 72 days.

(21) Appl. No.: 13/260,578

(22) PCT Filed: Apr. 5, 2010

(86) PCT No.: PCT/US2010/029899
§ 371 (c)(1),
(2), (4) Date: Sep. 27, 2011

(87) PCT Pub. No.: WO2010/117923
PCT Pub. Date: Oct. 14, 2010

(65) Prior Publication Data
US 2012/0029349 A1 Feb. 2, 2012

Related U.S. Application Data

(60) Provisional application No. 61/168,003, filed on Apr. 9, 2009.

(51) Int. Cl.
*A61M 5/00* (2006.01)
(52) U.S. Cl.
USPC .......................................... 600/432; 604/154
(58) Field of Classification Search
None
See application file for complete search history.

(56) References Cited

U.S. PATENT DOCUMENTS

| | | | |
|---|---|---|---|
| 2002/0038392 A1 | 3/2002 | De La Huerga | |
| 2003/0065287 A1 | 4/2003 | Spohn et al. | |
| 2005/0149358 A1 | 7/2005 | Sacco et al. | |
| 2008/0306443 A1* | 12/2008 | Neer et al. | 604/121 |
| 2009/0043607 A1 | 2/2009 | Nemoto et al. | |

FOREIGN PATENT DOCUMENTS

| | | |
|---|---|---|
| CN | 2619314 | 6/2004 |
| EP | 1433456 | 6/2004 |
| EP | 1723977 | 11/2006 |
| EP | 1782853 | 5/2007 |
| EP | 2000161 | 12/2008 |
| WO | 9965548 | 12/1999 |
| WO | 2006124775 | 11/2006 |

* cited by examiner

*Primary Examiner* — Unsu Jung
*Assistant Examiner* — Saurel J Selkin

(57) ABSTRACT

An injection device (120) used in delivering medical fluids to a patient is provided. The injection device (120) may include a syringe plunger driver (126a) and a syringe (140). The syringe (140) may include a syringe data storage device (134). The injection device (120) may include a communication device (132a) disposable in each of attached and detached conditions. The communication device (132a) may be operable to read a data storage device (134) within its field of view. When the communication device (132a) is attached to the injection device (120) and the syringe (140) is installed on the injection device (120), the communication device (132a) may be operable to read the data storage device (134) associated with the syringe (140). When in a detached condition, the communication device (132a) may be operable to be hand manipulated such that various other data storage devices (134) may be read.

15 Claims, 6 Drawing Sheets

MEDICAL FLUID DELIVERY SYSTEM WITH RFID-EQUIPPED WAND

RELATED APPLICATIONS

This application is a U.S. National Stage of PCT/US2010/029899, filed 5 Apr. 2010, which claims priority to and is a non-provisional application of U.S. Provisional Patent Application No. 61/168,003 filed on 9 Apr. 2009 entitled "MEDICAL FLUID DELIVERY SYSTEM WITH RFID-EQUIPPED WAND".

FIELD OF THE INVENTION

The present invention generally relates to medical fluid delivery systems and, more particularly, to medical fluid delivery systems that include devices that are capable of reading identification members.

BACKGROUND

Various medical procedures require that one or more medical fluids be injected into a patient. For example, medical imaging procedures oftentimes involve the injection of contrast media into a patient, possibly along with saline and/or other medical fluids. Other medical procedures involve injecting one or more medical fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

Radio Frequency Identification (RFID) tags are becoming more and more popular in various applications. RFID tags have been addressed in relation to medical applications, and including in relation to power injectors. For instance, it has at least been suggested to dispose an RFID tag on a power injector syringe and encode at least certain information onto such an RFID tag.

SUMMARY

A first aspect of the present invention is embodied by a medical fluid delivery system that includes an injection device and a communication device. The injection device includes a syringe plunger driver that in turn includes a motorized drive source. The injection device further includes a syringe having a syringe barrel and a syringe plunger movably disposed relative to the syringe barrel. The syringe plunger driver interacts with the syringe plunger to move the syringe plunger relative to the syringe barrel in at least a first direction. The syringe comprises a syringe data storage device. The communication device is disposable in each of attached and detached conditions relative to the injection device. The communication device includes a field of view. A data storage device within the field of view is communicable with the communication device. When the communication device is in the attached condition, it is disposed such that the syringe data storage device of the syringe is within the field of view.

A number of feature refinements and additional features are applicable to the first aspect of the present invention. These feature refinements and additional features may be used individually or in any combination. As such, each of the following features that will be discussed may be, but are not required to be, used with any other feature or combination of features of the first aspect. The following discussion is applicable to the first aspect, up to the start of the discussion of a second aspect of the present invention.

The communication device may include an electromagnetic communication device. The communication device may include an REID communication device. In an arrangement, the communication device may provide at least one of a read function and a write function. For example, the communication device may be operable to read from and/or write to an RFID tag.

When in the detached condition, the communication device may be movable such that the field of view is deployable about a data storage device of a patient and/or a data storage device of an operator of the medical fluid delivery system. In this regard, the communication device may be operable to read and/or write data to the data storage device of a patient and/or a data storage device of an operator while the communication device is in the detached condition. In an arrangement, the communication device may be operable to write data to the syringe data storage device, the data storage device of a patient, and/or the data storage device of an operator.

The communication device may include a power source operable to power the communication device when the communication device is in the detached condition. The communication device may include a memory unit that is operable to store data received by the communication device when the communication device is in the detached condition. The communication device may include a communication interface, and the communication device may be operable to send the stored data to the injection device via the communication interface when the communication device is in the attached condition. The communication interface may include a plurality of electrical contacts.

The medical fluid delivery system may further include a wiring arrangement interconnected to the communication device and the injection device. The communication device may be operable to communicate with the injection device via the wiring arrangement.

The communication device may include a syringe mount. In an embodiment, the injection device may include a syringe receiver, which in turn includes the communication device.

A second aspect of the present invention is embodied by a method of operation of a medical fluid delivery system. In this method, a first data storage device is read with a communication device. The reading includes hand-maneuvering the communication device proximate to the first data storage device. After reading the first data storage device, the communication device is attached to an injection device and then a syringe is installed on the injection device. The syringe includes a syringe data storage device. The communication device reads the syringe data storage device while the syringe is installed on the injection device and while the communication device is attached to the injection device.

A number of feature refinements and additional features are applicable to the second aspect of the present invention. These feature refinements and additional features may be used individually or in any combination. As such, each of the following features that will be discussed may be, but are not required to be, used with any other feature or combination of features of the second aspect. The following discussion is applicable to the second aspect, up to the start of the discussion of the term "field of view."

In an embodiment of the second aspect, the first data storage device may be attached to a patient and the step of reading a first data storage device may include moving the communication device proximate to the patient. The method may include detaching the communication device from the injection device prior to the step of reading a patient data storage device.

The method may further include reading a tubing set data storage device with the communication device. The data read from the tubing set data storage device may be used to set a pressure limit for the injection device. The communication device may store data acquired during reading within the communication device. Such data may include the data read from a patient data storage device and/or a tubing set data storage device.

The method may further include verifying medical fluid from the syringe is appropriate for injection into a patient. Such verifying may take into account data read from the patient data storage device and/or the syringe data storage device. A battery of the communication device may be recharged while the communication device is attached to the injection device. The method may further include wirelessly transferring data from the communication device to the injection device.

The attaching of the communication device to the injection device may include interconnecting the communication device to the injection device via a at least one conductive pathway. The method may further include transferring data from the communication device to the injection device while the communication device is attached to the injection device (e.g., through the at least one conductive pathway and/or through an inductive coupling).

The method may further include reading an operator data storage device with the communication device. Such reading may include downloading an injection protocol from the operator data storage device to the communication device. The method may further include selecting an injection protocol from a plurality of injection protocols resident in the injection device based at least in part on data obtained from the operator data storage device. The method may further include executing the injection protocol to inject the medical fluid from the syringe into the patient.

As used herein, the term "field of view," when used in relation to a communication device, denotes a region proximate to the communication device where a data storage device in that region will be readable and/or writable by the communication device.

A number of feature refinements and additional features are separately applicable to each of above-noted first and second aspects of the present invention. These feature refinements and additional features may be used individually or in any combination in relation to each of the above-noted first and second aspects. Any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a power injector includes "a syringe" alone does not mean that the power injector includes only a single syringe). Moreover, any failure to use phrases such as "at least one" also does not limit the corresponding feature to the singular (e.g., indicating that a power injector includes "a syringe" alone does not mean that the power injector includes only a single syringe). Finally, use of the phrase "at least generally" or the like in relation to a particular feature encompasses the corresponding characteristic and insubstantial variations thereof (e.g., indicating that a syringe barrel is at least generally cylindrical encompasses the syringe barrel being cylindrical).

Any "logic" that may be utilized by any of the various aspects of the present invention may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. This logic may be implemented at any single location or at multiple locations that are interconnected in any appropriate manner (e.g., via any type of network).

Any power injector that may be utilized to provide a fluid discharge may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading and/or drawing of fluid and/or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time. One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

Any such power injector may be used for any appropriate application where the delivery of one or more medical fluids is desired, including without limitation any appropriate medical application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging). Any such power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with any such power injector in any appropriate manner (e.g., detachably; front-loaded; rear-loaded; side-loaded), any appropriate medical fluid may be discharged from a given syringe of any such power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., medical tubing set), where this conduit is fluidly interconnected with the syringe in any appropriate manner and directs fluid to a desired location (e.g., to a catheter that is inserted into a patient for injection). As used herein, the term "fluidly interconnected" describes a relationship between components or entities where fluid is operable to flow in a predetermined flow path between the components or entities. For example, "an injection device fluidly interconnected to a patient" describes a configuration where fluid can flow from the injection device through any interconnecting devices (e.g., tubing, connectors) and into the patient (e.g., into the vasculature of the patient). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injector's syringe plunger drive assembly such that the syringe plunger drive assembly is able to advance the plunger in at least one direction, and possibly in two different, opposite directions.

DETAILED DESCRIPTION

Figure 1:
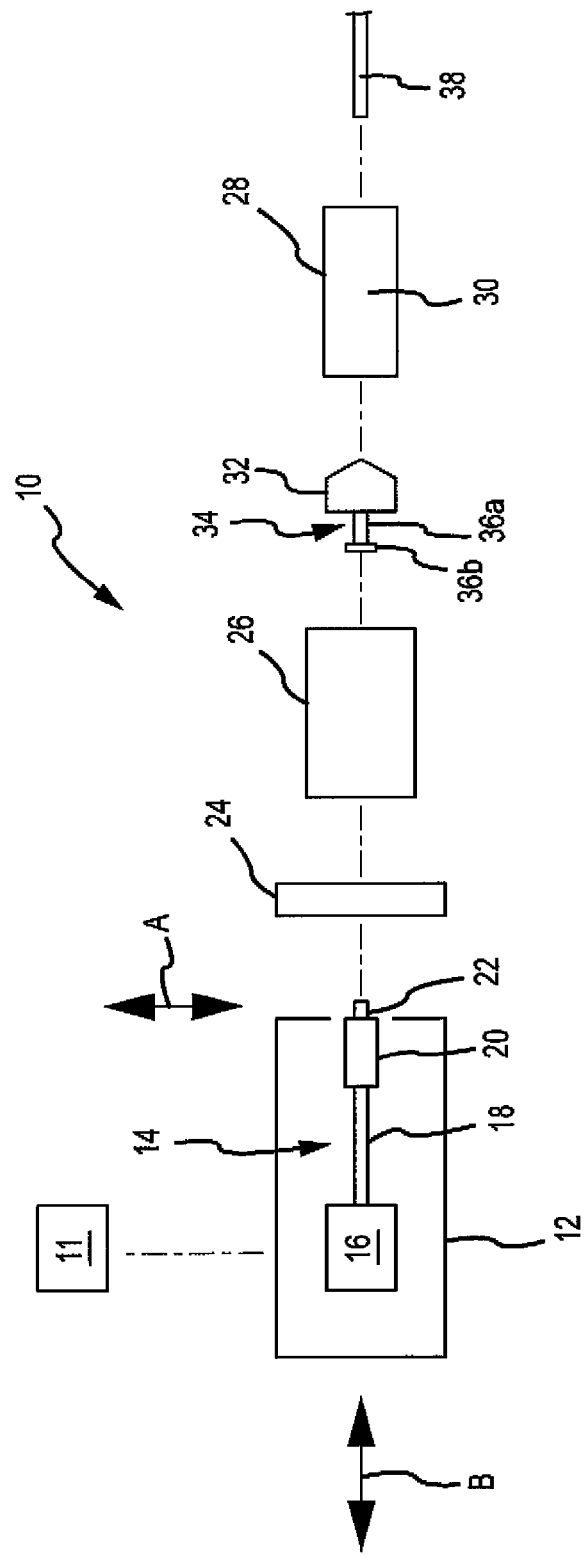
FIG. 1 is a schematic of one embodiment of a power injector.

FIG. 1 presents a schematic of one embodiment of a power injector 10 having a powerhead 12. One or more graphical user interlaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide any of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on the powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, these components may or may not be coupled when the ram 20 advances the syringe plunger 32 to discharge fluid from the syringe 28 (e.g., the ram 20 may simply "push on" the syringe plunger coupler 34 or directly on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
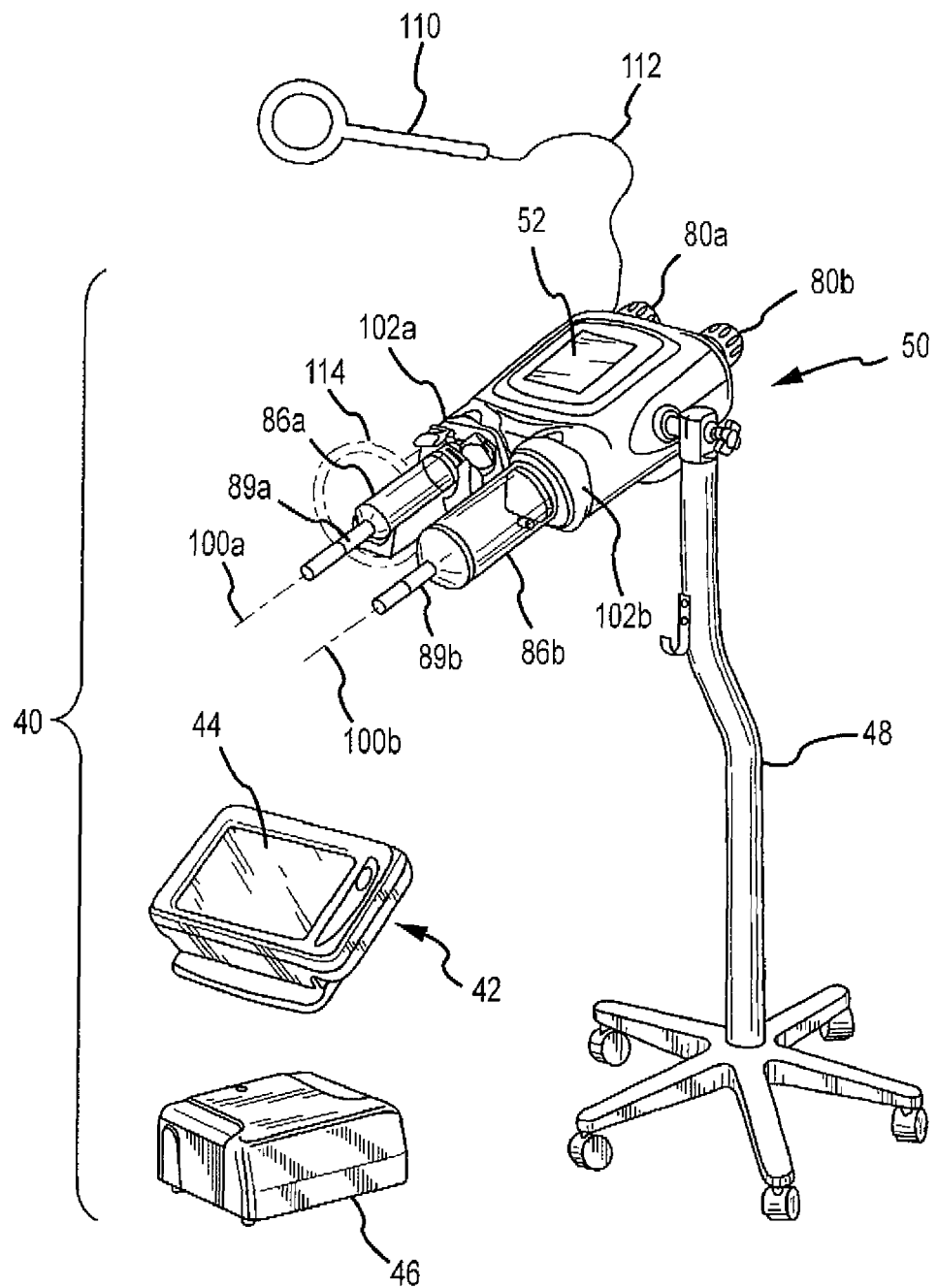
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 are mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one or more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Various details regarding the integration of the syringes 86a, 86b with the powerhead 50 are presented in FIG. 28. Each of the syringes 86a, 86b includes the same general components. The syringe 86a includes plunger or piston 90a that is movably disposed within a syringe barrel 88a. Movement of the plunger 90*a* along an axis 100*a* (FIG. 2A) via operation of the powerhead 50 will discharge fluid from within a syringe barrel 88*a* through a nozzle 89*a* of the syringe 86*a*. An appropriate conduit (not shown) will typically be fluidly interconnected with the nozzle 89*a* in any appropriate manner to direct fluid to a desired location (e.g., a patient). Similarly, the syringe 86*b* includes plunger or piston 90*b* that is movably disposed within a syringe barrel 88*b*. Movement of the plunger 90*b* along an axis 100*b* (FIG. 2A) via operation of the powerhead 50 will discharge fluid from within the syringe barrel 88*b* through a nozzle 89*b* of the syringe 86*b*. An appropriate conduit (not shown) will typically be fluidly interconnected with the nozzle 89*b* in any appropriate manner to direct fluid to a desired location (e.g., a patient).

The syringe 86*a* is interconnected with the powerhead 50 via an intermediate faceplate 102*a*. This faceplate 102*a* includes a cradle 104 that supports at least part of the syringe barrel 88*a*, and which may provide/accommodate any additional functionality or combination of functionalities. A mounting 82*a* is disposed on and is fixed relative to the powerhead 50 for interfacing with the faceplate 102*a*. A ram coupler 76 of a ram 74 (FIG. 2C), which are each part of a syringe plunger drive assembly or syringe plunger driver 56 (FIG. 2C) for the syringe 86*a*, is positioned in proximity to the faceplate 102*a* when mounted on the powerhead 50. Details regarding the syringe plunger drive assembly 56 will be discussed in more detail below in relation to FIG. 2C. Generally, the ram coupler 76 may be coupled with the syringe plunger 90*a* of the syringe 86*a*, and the ram coupler 76 and ram 74 (FIG. 2C) may then be moved relative to the powerhead 50 to move the syringe plunger 90*a* along the axis 100*a* (FIG. 2A). It may be such that the ram coupler 76 is engaged with, but not actually coupled to, the syringe plunger 90*a* when moving the syringe plunger 90*a* to discharge fluid through the nozzle 89*a* of the syringe 86*a*.

The faceplate 102*a* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*a* on and remove the faceplate 102*a* from its mounting 82*a* on the powerhead 50. The faceplate 102*a* may be used to couple the syringe plunger 90*a* with its corresponding ram coupler 76 on the powerhead 50. In this regard, the faceplate 102*a* includes a pair of handles 106*a*. Generally and with the syringe 86*a* being initially positioned within the faceplate 102*a*, the handles 106*a* may be moved to in turn move/translate the syringe 86*a* at least generally within a plane that is orthogonal to the axes 100*a*, 100*b* (associated with movement of the syringe plungers 90*a*, 90*b*, respectively, and illustrated in FIG. 2A). Moving the handles 106*a* to one position moves/translates the syringe 86*a* (relative to the faceplate 102*a*) in an at least generally downward direction to couple its syringe plunger 90*a* with its corresponding ram coupler 76. Moving the handles 106*a* to another position moves/translates the syringe 86*a* (relative to the faceplate 102*a*) in an at least generally upward direction to uncouple its syringe plunger 90*a* from its corresponding ram coupler 76.

The syringe 86*b* is interconnected with the powerhead 50 via an intermediate faceplate 102*b*. A mounting 82*b* is disposed on and is fixed relative to the powerhead 50 for interfacing with the faceplate 102*b*. A ram coupler 76 of a ram 74 (FIG. 2C), which are each part of a syringe plunger drive assembly 56 for the syringe 86*b*, is positioned in proximity to the faceplate 102*b* when mounted to the powerhead 50. Details regarding the syringe plunger drive assembly 56 again will be discussed in more detail below in relation to FIG. 2C.

Generally, the ram coupler 76 may be coupled with the syringe plunger 90*b* of the syringe 86*b*, and the ram coupler 76 and ram 74 (FIG. 2C) may be moved relative to the powerhead 50 to move the syringe plunger 90*b* along the axis 100*b* (FIG. 2A). It may be such that the ram coupler 76 is engaged with, but not actually coupled to, the syringe plunger 90*b* when moving the syringe plunger 90*b* to discharge fluid through the nozzle 89*b* of the syringe 86*b*.

The faceplate 102*b* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*b* on and remove the faceplate 102*b* from its mounting 82*b* on the powerhead 50. The faceplate 102*b* also may be used to couple the syringe plunger 90*b* with its corresponding ram coupler 76 on the powerhead 50. In this regard, the faceplate 102*b* may include a handle 106*b*. Generally and with the syringe 86*b* being initially positioned within the faceplate 102*b*, the syringe 86*b* may be rotated along its long axis 100*b* (FIG. 2A) and relative to the faceplate 102*b*. This rotation may be realized by moving the handle 106*b*, by grasping and turning the syringe 86*b*, or both. In any case, this rotation moves/translates both the syringe 86*b* and the faceplate 102*b* at least generally within a plane that is orthogonal to the axes 100*a*, 100*b* (associated with movement of the syringe plungers 90*a*, 90*b*, respectively, and illustrated in FIG. 2A). Rotating the syringe 86*b* in one direction moves/translates the syringe 86*b* and faceplate 102*b* in an at least generally downward direction to couple the syringe plunger 90*b* with its corresponding ram coupler 76. Rotating the syringe 86*b* in the opposite direction moves/translates the syringe 86*b* and faceplate 102*b* in an at least generally upward direction to uncouple its syringe plunger 90*b* from its corresponding ram coupler 76.

Figure 2B:
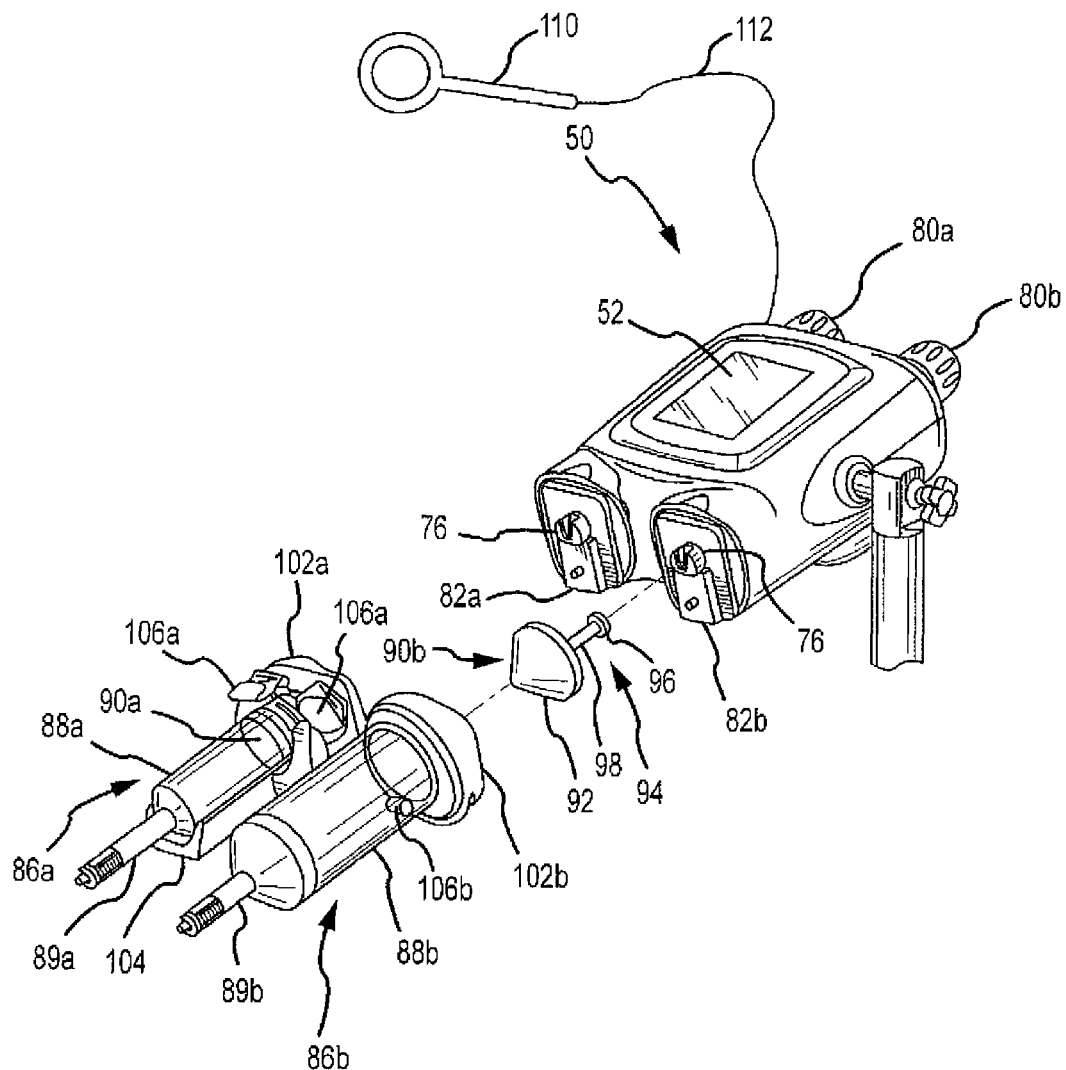
FIG. 2B is an enlarged, partially exploded, perspective view of a powerhead used by the power injector of FIG. 2A.

As illustrated in FIG. 2B, the syringe plunger 90*b* includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90*b* and its corresponding ram coupler 76 are in a coupled state or condition. The syringe plunger 90*a* may include a similar syringe plunger coupler 94 for interfacing with its corresponding ram coupler 76.

Figure 2C:
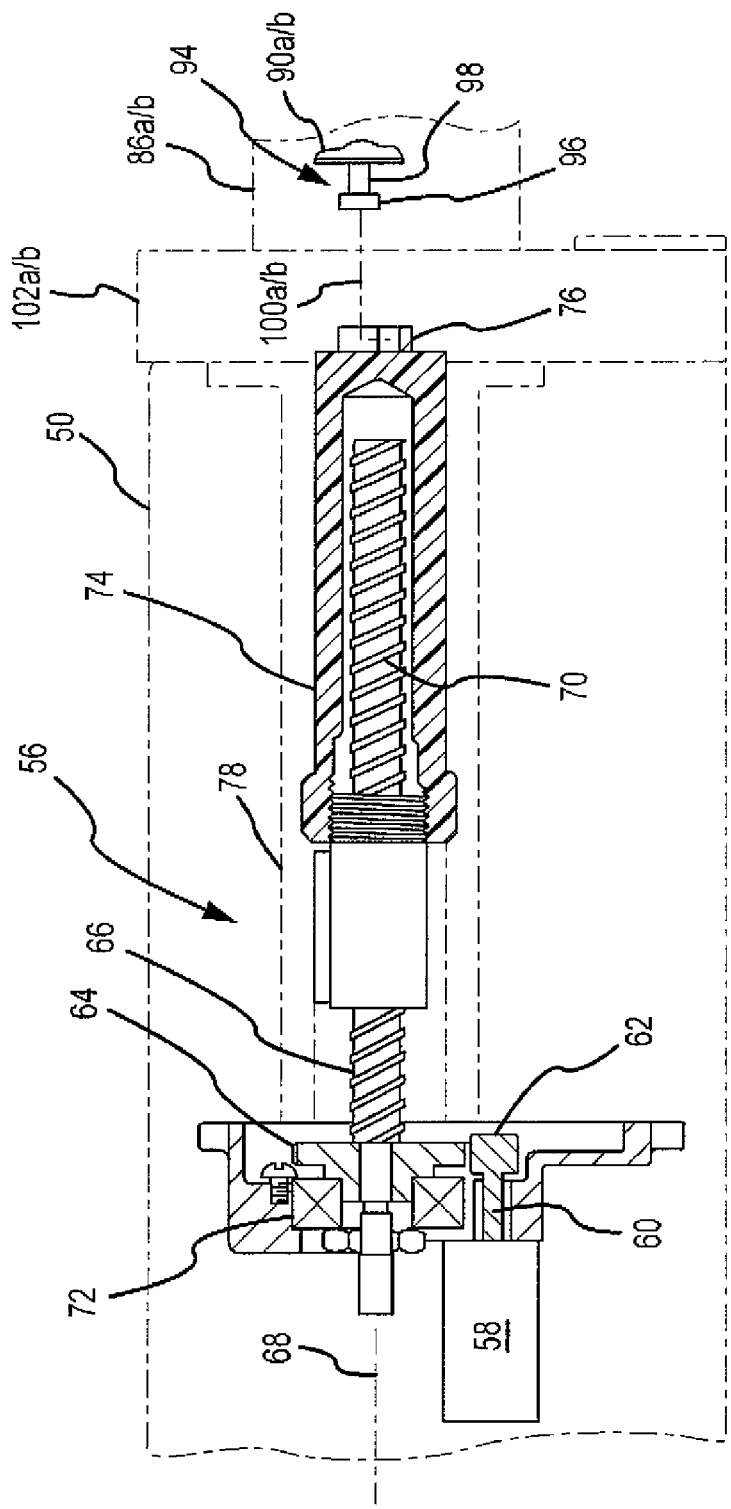
FIG. 2C is a schematic of one embodiment of a syringe plunger drive assembly used by the power injector of FIG. 2A.

The powerhead 50 is utilized to discharge fluid from the syringes 86*a*, 86*b* in the case of the power injector 40. That is, the powerhead 50 provides the motive force to discharge fluid from each of the syringes 86*a*, 86*b*. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86*a*, 86*b*. A separate syringe plunger drive assembly 56 may be incorporated into the powerhead 50 for each of the syringes 86*a*, 86*b*. In this regard and referring back to FIGS. 2A-B, the powerhead 50 may include hand-operated knobs 80*a* and 80*b* for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86*a/b*, while rotation of the drive screw 66 in the opposite direction axially advances the ram 74 along the drive screw 66 (and thereby along axis 68) away from the corresponding syringe 86*a/b*. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90*a/b* of the corresponding syringe 86*a/b*. When the ram coupler 76 and syringe plunger coupler 94 are appropriately coupled, the syringe plunger 90*a/b* moves along with ram 74. FIG. 2C illustrates a configuration where the syringe 86*a/b* may be moved along its corresponding axis 100*a/b* without being coupled to the ram 74. When the syringe 86*a/b* is moved along its corresponding axis 100*a/b* such that the head 96 of its syringe plunger 90*a/b* is aligned with the ram coupler 76, but with the axes 68 still in the offset configuration of FIG. 2C, the syringe 86*a/b* may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation computed tomography or CT imaging, magnetic resonance imaging or MRI, single photon emission computed tomography or SPECT imaging, positron emission tomography or PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation singlehead configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Returning to FIGS. 2A and 2B, a communication device in the form of a wand 110 may be interconnected to the power injector 40. The wand 110, along with associated control electronics, may be operable to communicate with various data storage devices that may be associated with injecting medical fluids into a patient using the power injector 40. The wand 110 can use any appropriate technology for communicating with the various data storage devices. The associated control electronics may be disposed in any appropriate location (e.g., within the wand 110 and/or within the powerhead 50). The data storage devices may be of any appropriate construction including RFID tags, barcodes, and/or other types of identifying features. Such data storage devices may be disposed on, and/or associated with, various components used during an injection process. Accordingly, the wand 110 may be an electromagnetic communication device capable of electromagnetically reading data from, and/or writing data to, an appropriate data storage device. For example, the wand 110 may be an RFID tag communication device.

The wand 110 may be operable to be hand-held and handmanipulated to position the wand 110 proximate to various data storage devices. For example, a user of the wand 110 may move the wand 110 such that it is proximate to an identification data storage device (e.g., an RFID identification bracelet) associated with a patient who is to receive an injection of medical fluid using the power injector 40. The "user" may be any appropriate personnel who may participate in the process of injecting medical fluid into a patient. Accordingly, a user may include an imaging technician, nurse, doctor, and/or any other appropriate medical personnel. When not being used in a hand-held fashion, the wand 110 may be attached to the powerhead 50 in a mounted position 114 illustrated in FIG. 2A with dashed lines.

The wand 110 may be operatively interconnected to the powerhead 50 in any appropriate manner. For example, the wand 110 may be interconnected to the powerhead 50 via a wiring arrangement 112. The wiring arrangement 112 may be operable to transmit data and/or power between the wand 110 and the powerhead 50. The wiring arrangement 112 may be in any appropriate form and include any appropriate number of conductors. For example, the wiring arrangement 112 may include one or more cables and/or a wiring harness that may include a plurality of separately insulated conductive pathways. The wand 110 operatively interconnected to the powerhead 50 via the wiring arrangement 112 may be operable to store data read (e.g., read from data storage devices) and subsequently download such data via the wiring arrangement 112 at any appropriate time.

In an arrangement, the wand 110 may be a wireless communication device. In one implementation of such an arrangement, the wand 110 may be operable to wirelessly communicate with the powerhead 50 using any appropriate wireless communication technology (e.g., Bluetooth, Wi-Fi). In another implementation of such an arrangement, the wand 110 may be operable to store data read (e.g., read from data storage devices) while being used in a hand-held fashion and subsequently download such data when attached to the powerhead 50 in the mounted position 114. When attached in the mounted position 114, the wand 110 may be mechanically and/or communicatively interconnected to the powerhead 50. The communicative interconnection may be of any appropriate form including, for example, direct electrical interconnection and inductive interconnection. In a wireless arrangement, the wand 110 may be powered in any appropriate manner. When mounted, the wand 110 may be operable to receive power from the powerhead 50 using, for example, a direct electrical interconnection and/or an inductive coupling. Such received power may be used to charge batteries and/or capacitors of the wand 110, which may then be used to power the wand 110 during hand-held operation.

The data storage devices that may be scanned by the wand 110 may be disposed on and/or associated with any part, device, and/or personnel described herein. For example, the data storage devices may be attached to, or be a part of, the user's identification badge, a patient's identification bracelet, disposables (e.g., tubing set, catheter), an area (e.g., a patient room), a pharmaceutical, a bulk fluid container (e.g., saline, contrast), the powerhead 50, and/or the syringes 86a/b (including both empty and filled types). For such items, the wand 110 may be moved so that the wand 110 is proximate to the associated data storage devices. Furthermore, the wand 110, when in the mounted position 114, may be operable to scan specific items used in the injection process. For example, when in the mounted position 114, the wand 110 may be operable to read and/or write to an RFID tag of the syringe 86a installed on the powerhead 50.

Data storage devices discussed herein may contain any appropriate information. For example, a patient identification data storage device may contain identification information for the patient and additional information such as drug allergies, preferred injection protocols, and/or other information. In another example, a user identification badge may contain injection protocols preferred by that user.

Figure 3:
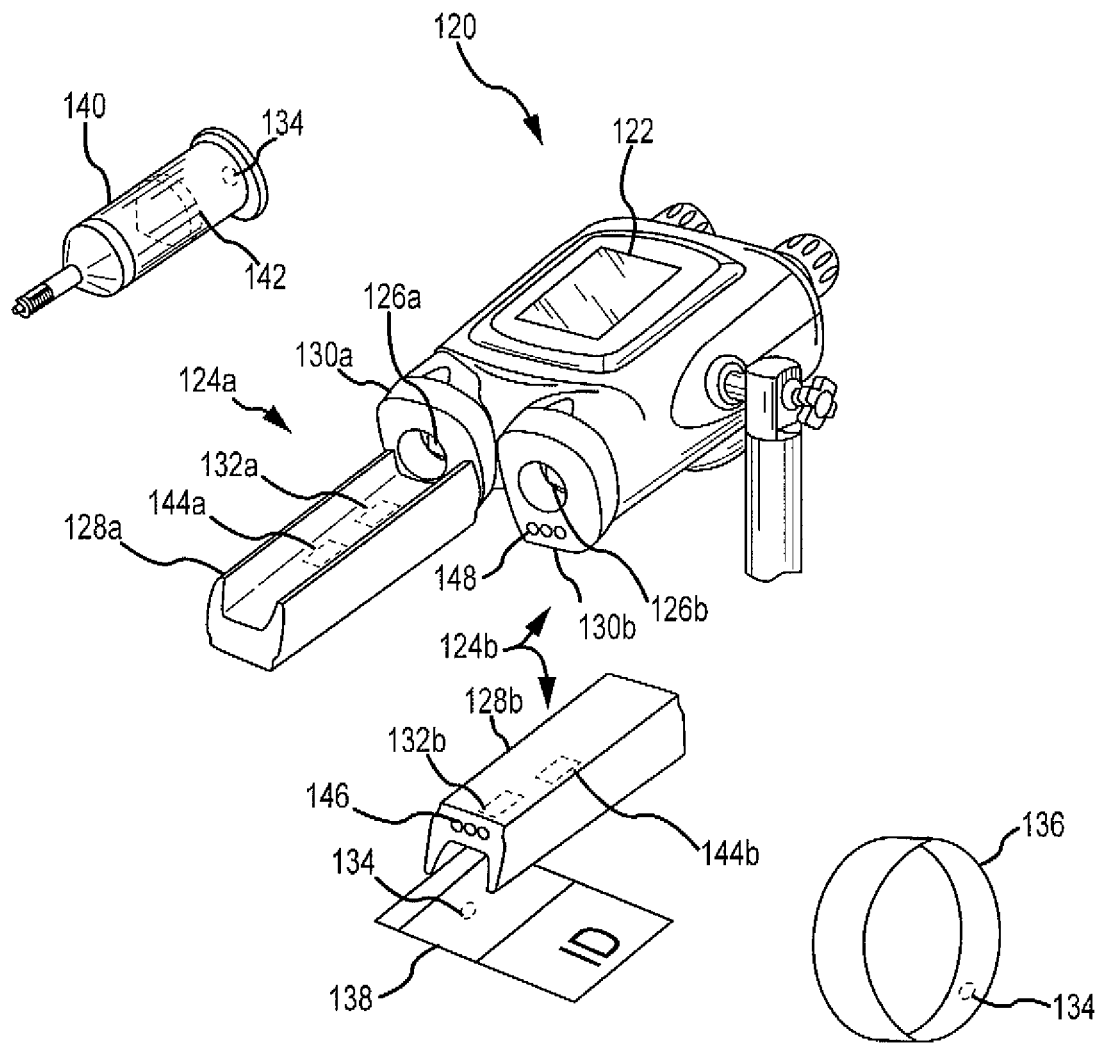
FIG. 3 is a perspective view of an injection device that includes a syringe mount with a wand portion.

FIG. 3 is a perspective view of an injection device 120 that includes syringe mounts 124a/b. The injection device 120 may be in the form of a powerhead such as the powerhead 50 discussed above. The injection device 120 may include syringe plunger drivers 126a/b capable of interfacing with a plunger 142 of a syringe 140. The syringe plunger drivers 126a/b of the injection device 120 may include a motorized drive source associated with the injection device 120.

The syringe mounts 124 a/b may be of any appropriate size, shape, configuration, and/or type. In the illustrated embodiment, the syringe mounts 124 a/b are appropriately mounted on or otherwise integrated with the injection device 120 to provide an interface between the syringe 140 and the injection device 120. A portion of the syringe mounts 124 a/b may be permanently attached to or incorporated by the injection device 120, or at least installed thereon with proper tooling. The syringe mounts 124 a/b may also be in the form of an adapter to allow different configurations of syringes 140 to be installed on the injection device 120 (e.g., an adapter may be installed on a syringe interface structure on the injection device 120 so a different syringe may be used—one syringe may be used with the syringe interface structure of the injection device 120, and another syringe may be used when an appropriate adapter is installed on the injection device 120). The syringe mounts 124 a/b may also be in the form of a faceplate to which one or more configurations of syringes 140 may be installed, and which may be installed on the injection device 120 without any tooling (e.g., simply by hand). In this case, it may be such that a faceplate is required to install any syringe 140 on the injection device 120—the syringe 140 could not be installed on the injection device 120 without the faceplate in this instance.

The syringe mounts 124a/b may be removably attached to the injection device 120. The syringe mounts 124a/b may be attached and detached from the injection device 120 in a manner similar to the attachment of faceplates 102a/b to the powerhead 50 discussed above with reference to FIGS. 2A through 2C. The embodiment of FIG. 3 contains two syringe mounts 124a/b: a syringe mount 124a attached to a syringe plunger driver 126a and a syringe mount 124b partially attached to a syringe plunger driver 126b. In other arrangements, the injection device 120 may include a single syringe plunger driver 126a/b or more than two syringe plunger drivers 126a/b. In an arrangement, each of the syringe plunger drivers 126a/b of the injection device 120 may have a syringe mount 124a/b attached thereto, or a portion of the syringe plunger drivers 126a/b of the injection device 120 may have a syringe mount 124a/b attached thereto. The syringe mount 124a/b may be operable to hold or receive the syringe 140 in a manner similar to that described above with respect to intermediate faceplates 102a/b and syringes 86a.

Syringe mount 124a may include a wand portion 128a and a base portion 130a. The base portion 130a may be operable to attach to the injection device 120 in a manner similar to the attachment of the faceplate 102a/b to the powerhead 50 described above with reference to FIGS. 2A through 2O. The base portion 130a may be communicatively interconnected to the injection device 120 when the base portion 130a is attached to the injection device 120. Such an interconnection may be achieved through a direct electrical interconnection between electrically conductive pathways of the base portion 130a and corresponding conductive pathways of the injection device 120 (e.g., mating electrical connectors and/or contacts that become electrically interconnected upon attachment of the base portion 130 to the injection device 120). In another example, a wiring arrangement (not shown) may extend from the base portion 130a and be operable to be plugged into a corresponding connector on the injection device 120. Alternatively, the base portion 130a may be communicatively interconnected to the injection device 120 through an inductive coupling when the base portion 130a is attached to the injection device 120. Any other appropriate type of communicative interconnection may be utilized. As noted above, the syringe mounts 124a/b may be operable to hold or receive the syringe 140. In this regard, the wand portion 128a and/or the base portion 130a of the syringe mount 124a may include features allowing the syringe 140 to be mounted thereto.

The wand portion 128a may be operable to be attached (e.g., docked) and detached from the base portion 130a. Such attaching and detaching may be performed without the use of tools (e.g., the wand portion 128a may be attachable and detachable from the base portion 130a by hand). The wand portion 128a may attach to the base portion 130a in any appropriate manner. For example, a groove on the wand portion 128a may slide onto a corresponding protruding member on the base portion 130a and snap into place. Other methods, such as magnetic coupling and/or latches may be used to secure the wand portion 128a to the base portion 130a.

The wand portion 128a may include a communication device 132a. The communication device 132a may be a device operable to read from and/or write to data storage devices 134 that may be attached to various objects associated with the injection of medical fluids into a patient, such as those described above with reference to the wand 110 of FIG. 2A. For example, the communication device 132a may be an RFID communication device capable of reading and/or writing to an RFID tag. The communication device 132a may have a field of view. As used herein, the term "field of view" denotes a region proximate to a communication device (e.g., communication device 132a of wand portion 128a, wand 110 of FIG. 2A) where the data storage device 134 in that region will be communicable with that communication device (e.g., where the data storage device 134 is readable by that communication device and/or the communication device will be operable to write to the data storage device 134). When attached to the base portion 130a, the wand portion 128a, in addition to being mechanically interconnected to the base portion 130a, may be electrically and/or communicatively interconnected to the base portion 130a. The wand portion 128a may be operable to communicate with the base portion 130a in that the wand portion 128a may be able to transfer data obtained from the communication device 132a to the base portion 130a. The wand portion 128a may also be operable to receive data from the base portion 130a and use such data to write to an RFID tag within the field of view of the wand portion 128a. By virtue of the communicative interconnection between the wand portion 128a and the base portion 130a and the communicative interconnection between the base portion 130a and the injection device 120 (discussed above), the wand portion 128a may be operable to communicate with the injection device 120. When attached to the base portion 130a, the field of view of the communication device 132a of the wand portion 128a may be disposed such that it is able to read and/or write to the data storage device 134 on the syringe 140 installed on the syringe mount 124a.

The communication between the wand portion 128a and the base portion 130a may occur in any appropriate manner. For example, when the wand portion 128a is attached to the base portion 130a, the two portions 128a, 130a may be directly electrically interconnected through corresponding sets of contacts on each portion 128a, 130a. Such an arrangement is illustrated on the wand portion 128b and base portion 130b of FIG. 3. The wand portion 128b includes a set of electrically conductive members 146 and the base portion 130b includes a corresponding set of electrically conductive members 148. The electrically conductive members 146, 148 are arranged such that they are communicatively interconnected when the wand portion 128b is mounted to the base portion 130b.

In another arrangement, the wand portion 128a may be operable to wirelessly communicate with the base portion 130a. Such wireless communication may occur in any appropriate manner using any appropriate technology. For example, such wireless communication may occur using optical means. In another example, such wireless communication may take place through an inductive coupling between the wand portion 128a and the base portion 130a when the wand portion 128a and is attached to the base portion 130a. In another example, such wireless communication may use a radio frequency (RF) wireless communication system such as Bluetooth®. In the latter example, the wireless communication between the base portion 130a and the wand portion 128a may be operable to occur when the wand portion 128a is detached from the base portion 130a.

The wand portion 128a may include a power source operable to power the wand portion 128a. The power source may, for example, include batteries disposed within the wand portion 128a. Such batteries may need to be removed and then replaced and/or recharged when their power is depleted. In another arrangement, the syringe mount 124a may include the ability to charge batteries within the wand portion 128a when the wand portion 128a is attached to the base portion 130a. In this regard, the injection device 120 may supply power to the base portion 130a, which in turn may include a direct electrical interconnection to the wand portion 128a through which power may be transferred to charge the batteries within the wand portion 128a. Alternatively, such power transfer between the wand portion 128a and the base portion 130a may occur through an inductive coupling. In a particular arrangement, both the communicative and power interconnections may occur wirelessly. For example, the communication between the wand portion 128a and the base portion 130a may utilize optical or RF means while power may be delivered to the base portion 130a via an inductive coupling. In another example, communication and power may occur through the same inductive coupling between the wand portion 128a and the base portion 130a. In an arrangement, the wand portion 128a may be powered by charged capacitors in place of the aforementioned batteries.

When the wand portion 128a is detached from the base portion 130a, it may be used to read and/or write to the various data storage devices 134 discussed above (e.g., RFID tags). The wand portion 128a may be moved proximate to the various data storage devices 134 to be scanned such that the data storage devices 134 are disposed within the wand portion's 128a field of view. Once information is scanned by the wand portion 128a, the information may be immediately downloaded to the injection device 120 via a wireless link. Such a wireless link may be through the base portion 130a or directly to a wireless communication module of the injection device 120. Alternatively, the scanned information may be temporarily stored within the wand portion 128a for later downloading once the wand portion 128a is attached to the base portion 130a. Accordingly, the wand portion 128a may include a memory unit 144a capable of storing scanned information. The wand portion 128b may also include a memory unit 144b capable of storing scanned information. The memory units 144a/b may also hold information that may be used to write to the various data storage devices 134 where appropriate.

The syringe mount 124b may be configured similarly to the syringe mount 124a described above. As illustrated in FIG. 3, the wand portion 128b may be detached from the base portion 130b and used to scan a user identification badge 138 and/or a patient identification bracelet 136 by manipulating the wand portion 128b such that the data storage device 134 of the item to be read and/or written to is within the field of view of the communication device 132b.

Although the embodiment of the syringe mount 124a/b of FIG. 3 utilizes a two-piece construction, in an alternate embodiment of the syringe mount 124a, the syringe mount 124a may be a unitary device. In such an embodiment, the entire syringe mount 124a may be removed from the injection device 120 when using the syringe mount 124a to the read and/or write to data storage devices 134 remote from the injection device 120. Such a unitary device may communicate with the injection device 120 in a manner similar to the communication between the base portion 130a and the injection device 120 and/or between the wand portion 128a and the base portion 130a described above.

When the wand portion 128a is attached to the base portion 130a (or in a unitary syringe mount 124a embodiment), the syringe mount 124a may be operable to position and/or support a syringe 140 installed thereon. In this respect, the syringe mount 124a may perform the same functions as the previously discussed faceplates 102a/b. Furthermore, the various features of the previously discussed faceplates 102a/b may be incorporated into the syringe mount 124a/b. Additional features, such as syringe heaters operable to heat fluid within an installed syringe 140 may also be incorporated into the syringe mounts 124a/b.

The syringes 140 to be installed onto the syringe mount 124a and used by the injection device 120 may contain one or more data storage devices 134 of any appropriate type and using any appropriate data storage technology (e.g., RFID tags). Such data storage devices 134 may be capable of storing information such as content type, concentration, manufacture date and/or lot, expiration date, date filled, fill volume and/or any other appropriate information. Furthermore, the data storage devices 134 on the syringes 140 may be operable to have information written thereon by the communication device 132a/b. Any appropriate number of data storage devices 134 may be associated with a given syringe 140. A data storage device 134 may be incorporated at any appropriate location on the syringe 140

Figure 4:
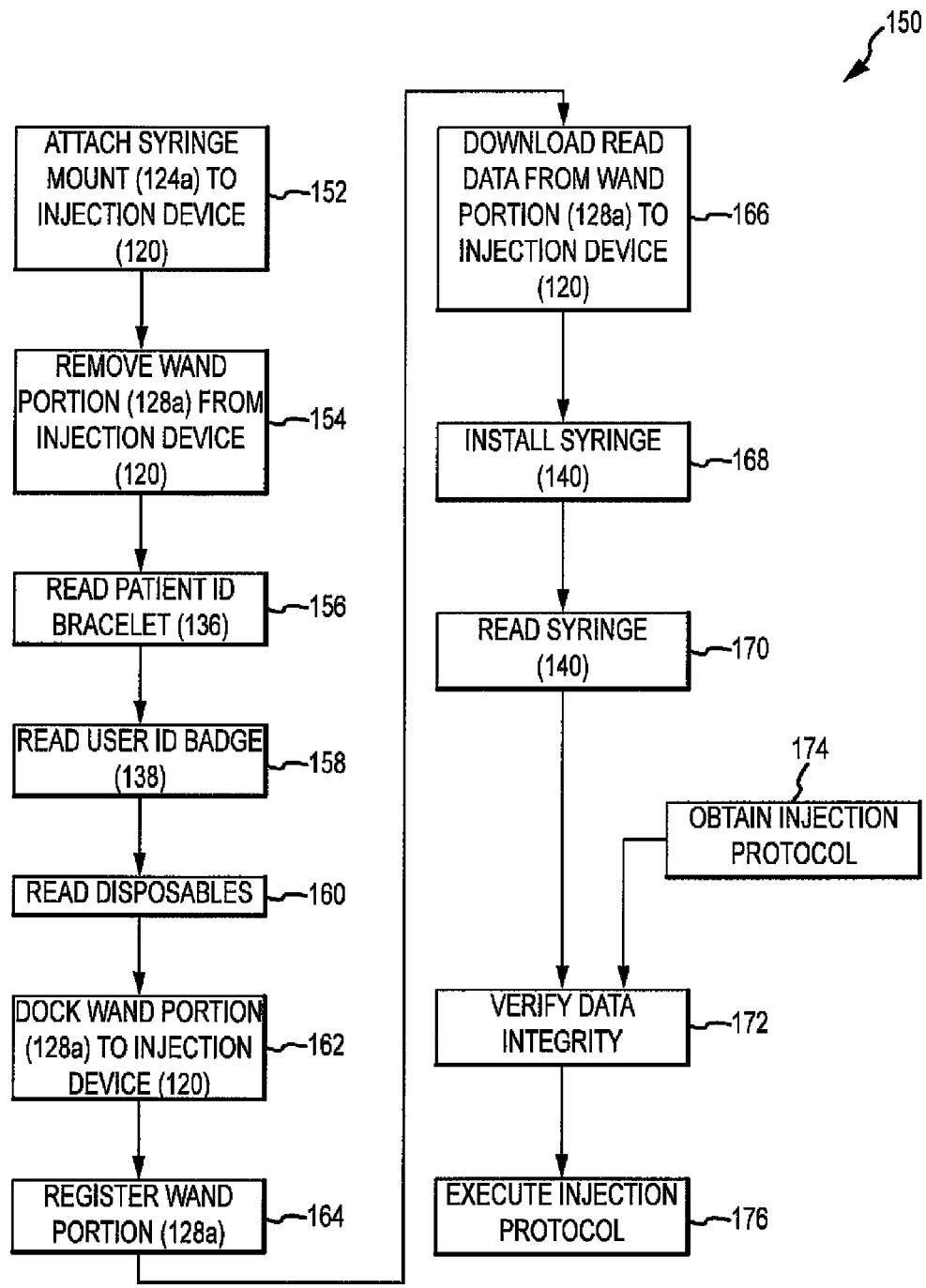
FIG. 4 is a flowchart of a method of injecting a patient with medical fluid using the injection device of FIG. 3.

FIG. 4 is a flowchart of a method 150 of operation of the injection device 120 of FIG. 3. The first step 152 of the method 150 may be to install the syringe mount 124a onto the injection device 120. The step 152 may further include electrically interconnecting the syringe mount 124a to the injection device 120 by, for example, plugging an electrical connector of the syringe mount 124a into a corresponding connector of the injection device 120. In an alternate embodiment, the electrical interconnection between the syringe mount 124a and the injection device 120 may occur when the syringe mount 124a is installed onto the injection device 120.

The next step 154 may be to remove the wand portion 128a from the injection device 120. This may include separating the wand portion 128a from the base portion 130a. Such separation may be performed by hand by a user of the injection device 120. Separation may be achieved by pulling the wand portion 128a away from the base portion 130a with enough force to overcome a retention force due to, for example, a magnetic interconnection and/or mechanical interconnection between the wand portion 128a and the base portion 130a. In an embodiment, a latch and/or clamp may be undone and/or a button may be pressed to separate the wand portion 128a from the base portion 130a.

The user may next use the wand portion 128a to read the data storage device 134 associated with patient identification bracelet 136 (e.g., worn by a patient to receive an injection). Generally, the present method 150 is described in terms of reading data from particular items with the wand portion 128a. It will be appreciated that all reading steps described in the present method 150 may include writing data to the particular item, either in combination with the described reading or in place of the described reading. The step 156 may incorporate positioning the wand portion 128a proximate to the patient identification bracelet 136. The wand portion 128a may be in the form of an electromagnetic device capable of electromagnetically reading data from and/or writing data to the appropriate data storage device 134. In this regard, the wand portion 128a may be operable to read the RFID tag 134 interconnected to the patient identification bracelet 136. The wand portion 128a may emit an audible tone to indicate a successful read of the patient identification bracelet 136. Other indicators of a successful read by the wand portion 128a, such as a light on the wand portion 128a, may be used in addition to or in place of the audible tone. The wand portion 128a may store the data read from the patient identification bracelet 136 in the memory unit 144a. The data read may include patient name, a patient identification number, patient drug allergies, a preferred injection protocol, and/or any other appropriate information. In an embodiment where the wand portion 128a includes wireless communication capabilities, the wand portion 128a may immediately wirelessly transmit the data read from the patient identification bracelet 136 to the base portion 130a and/or the injection device 120.

The next step 158 may be to use the wand portion 128a to read the data storage device 134 associated with the user identification badge 138. This may be performed by moving the wand portion 128a proximate to the identification badge 138 as illustrated in FIG. 3. The information read from the user identification badge 138 may include the users name and/or other user identifier, an injection protocol preferred by the user, and/or any other appropriate information. The read information may be stored locally and/or transmitted such as with the information read during step 156. This information may further be used to prevent unauthorized activation of the injection device 120.

This may be followed by the step 160 of using the wand portion 128a to read data storage devices attached to and/or associated with disposables to be used in the injection process. Such disposables may include, for example, a tubing set and a catheter. The information read from the disposables may include the part numbers, manufacturing information, performance characteristics (e.g., maximum pressure ratings), and/or any other appropriate information. The read information may be stored locally and/or transmitted such as with the information read during step 156.

Additional items beyond those discussed with reference to steps 156, 158 and 160, may be read by the user using the wand portion 128a. Such items may include pharmaceuticals, identification badges of additional personnel present, and/or any other appropriate. Furthermore, the above-described order in which the various items are read by the wand portion 128a may be altered. Moreover, for a particular injection process, not all of the above-described steps of reading items with the wand portion 128a need be performed.

After the reading steps 156, 158 and 160 are completed, the next step 162 may be to dock the wand portion 128a to the injection device 120. This may entail attaching the wand portion 128a to the base portion 130a. The next step 164 may be to register the wand portion 128a to the base portion 130a and/or the injection device 120. Registering the wand portion 128a may entail establishing a communication link between the wand portion 128a and the base portion 130a and/or injection device 120. Registering the wand portion 128a may also confirm that the wand portion 128a is the correct wand portion 128a for the base portion 130a. Once registered, the next step 166 may be performed. Step 166 may include downloading the data read by the wand portion 128a during steps 156, 158 and 160 from the wand portion 128a to the base portion 130a and/or the injection device 120. Once docked, the wand portion 128a may draw power from the base portion 130a to charge an energy storage device (e.g., battery) of the wand portion 128a.

The next step 168 may be to install a syringe 140 into the syringe mount 124a, Installing of the syringe 140 may include interconnecting a plunger 142 of the syringe 140 to the syringe plunger driver 126a. Once connected, the injection device 120 may be operable to drive (e.g., advance and/or retract) the plunger 142 of the syringe 140. Step 168 may also include interconnecting any appropriate disposables such as a tubing set to the syringe 140.

The next step 170 may be for the wand portion 128a to read the data storage device 134 of the syringe 140 while the wand portion 128a is attached to the base portion 130a. In this regard, the syringe 140 may be loaded onto the syringe mount 124a such that the data storage device 134 of the syringe 140 is within the field of view of the communication device 132a of the wand portion 128a. The data read from the data storage device 134 of the syringe 140 may be forwarded to the injection device 120.

Once the data has been downloaded from the wand portion 128a and the data storage device 134 of the syringe 140 has been read, the next step 172 may be to verify the integrity of the data. Such verification may take the form of confirming that the various pieces of data are in agreement. For example, the data storage device 134 on the syringe 140 may contain information regarding the patient for which the syringe 140 is intended. This data may be compared with the identification of the patient obtained from the patient identification bracelet 136 to confirm that the correct medical fluid is being administered to the correct patient. Step 172 may also include verifying an injection protocol obtained in step 174.

The step 174 of obtaining an injection protocol may be performed in a variety of ways. For example, the injection protocol may be resident in the user identification badge 138 and may be downloaded during the reading of the user identification badge 138 of step 158. Alternatively, the injection protocol may be resident in the patient's identification bracelet 136 and may be downloaded during the reading of the patient identification bracelet 136 of step 156. Such a protocol may have been loaded onto the patient identification bracelet 136 by, for example, a prescribing doctor.

In another embodiment, the injection device 120 may include a plurality of injection protocols, and a user may select the injection protocol to be used from the plurality of injection protocols. Such selection may take the form of the user manually selecting and injection protocol (e.g., using a GUI 122 of the injection device 120) or, the injection device 120 may automatically select an injection protocol based on, for example, the user (e.g., obtained during the reading of the user identification badge 138 of step 158) and/or the liquid to be injected (e.g., obtained during the reading of the syringe 140 of step 170). The step 172 of verifying data integrity may also include verifying that aspects of the selected protocol (e.g., flow rates and pressures) are appropriate for the disposables (e.g., tubing set and/or catheter) to be used during the injection process. The step 172 of verifying data integrity may also include verifying that the user, medical fluids within the syringe 140, and the patient all are appropriate for the selected injection protocol.

The verification of data integrity of step 172 may be helpful in reducing the potential of injecting the wrong pharmaceutical into a patient, injecting an expired medical fluid into a patient, and/or using the wrong protocol for a particular patient and/or syringe. Furthermore, such information, along with any other information described herein that is read by the wand portion 128a, may be used for purposes in addition to its role in running an injection protocol. For example, such information may be used to track inventories, track billing, track equipment performance, track patient injection history, and/or track user activity. During the method 150, the injection device 120 may also interface with a local network (e.g., a hospital's network) to obtain, verify and/or upload information related to the injection procedure.

The next step 176 may be to execute the injection protocol. As part of, or prior to the execution of, the injection protocol, the injection device 120 and attached tubing may be purged of air and fluidly interconnected to the patient (e.g., through a tubing set and catheter). After such purging, the injection device 120 may inject medical fluid into the patient according to the injection protocol.

The method 150 has been described above with reference to injecting medical fluids from a single syringe 140 installed on syringe mount 124a. In another implementation of the method 150, a second syringe may be installed onto syringe mount 124b. For example, the syringe 140 installed on syringe mount 124a may be filed with contrast while a second syringe installed onto syringe mount 124b may be filled with saline. The injection protocol may call for the injection of both saline and contrast. Where the injection protocol calls for the injection of medical fluids from two separate syringes, each syringe mount 124a/b may read a data storage device 134 of a syringe installed on its respective syringe mount 124a/b. For the preceding reading steps where the wand portion 128a of the syringe mount 124a is detached from its base portion 130a in order to read various components, wand portion 128a and/or wand portion 128b may be used to complete such reading steps.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A method of operation of a medical fluid delivery system, said method comprising:
    reading a first data storage device with a communication device, wherein said reading step comprises hand-maneuvering said communication device proximate to said first data storage device and relative to an injection device;
    attaching said communication device to said injection device after said reading a first data storage device step;
    installing a syringe on said injection device after said attaching step, wherein said syringe comprises a syringe data storage device; and
    reading said syringe data storage device with said communication device while said syringe is installed on said injection device and while said communication device is attached to said injection device.

2. The method of claim 1, wherein said first data storage device is attached to a patient and said reading a first data storage device step comprises moving said communication device proximate to said patient.

3. The method of claim 1, further comprising detaching said communication device from said injection device prior to said reading a first data storage device step.

4. The method of claim 1, further comprising reading a tubing set data storage device with said communication device.

5. The method of claim 4, further comprising setting a pressure limit based on data read during said reading a tubing set data storage device step.

6. The method of claim 1, further comprising storing data, in said communication device, acquired during said reading a first data storage device step prior to said attaching step.

7. The method of claim 1, further comprising recharging a battery of said communication device while said communication device is attached to said injection device.

8. The method of claim 1, further comprising verifying medical fluid from said syringe is appropriate for injection into a patient, wherein said verifying step takes into account data read from said first data storage device and said syringe data storage device.

9. The method of claim 1, further comprising wirelessly transferring data from said communication device to said injection device.

10. The method of claim 1, wherein said attaching step comprises interconnecting said communication device to said injection device via at least one conductive pathway.

11. The method of claim 1, further comprising transferring data from said communication device to said injection device while said communication device is attached to said injection device.

12. The method of claim 1, further comprising reading an operator data storage device with said communication device.

13. The method of claim 12, wherein said reading an operator data storage device step comprises downloading an injection protocol from said operator data storage device to said communication device.

14. The method of claim 13, further comprising executing said injection protocol to discharge medical fluid from said syringe.

15. The method of claim 12, further comprising selecting an injection protocol from a plurality of injection protocols resident in said injection device based at least in part on data obtained from said operator data storage device.

* * * * *